United States Patent [19]

Tsuchida et al.

[11] Patent Number: 5,147,424
[45] Date of Patent: Sep. 15, 1992

[54] OXYGEN-PERMEABLE POLYMERIC MEMBRANES

[75] Inventors: Eishun Tsuchida; Hiroyuki Nishide, both of Tokyo; Hiroyoshi Kawakami, Hachioji, all of Japan

[73] Assignee: Union Carbide Industrial Gases Technology Corporation, Danbury, Conn.

[21] Appl. No.: 722,831

[22] Filed: Jun. 28, 1991

[51] Int. Cl.$^5$ ............................................. B01D 53/22
[52] U.S. Cl. .......................................... 55/158; 55/16
[58] Field of Search .................... 55/16, 68, 158

[56] References Cited

U.S. PATENT DOCUMENTS

| | | | |
|---|---|---|---|
| 3,957,504 | 5/1976 | Ho et al. | 55/16 X |
| 4,343,715 | 8/1982 | Bonaventura et al. | 55/68 X |
| 4,427,416 | 1/1984 | Bonaventura et al. | 55/68 X |
| 4,451,270 | 5/1984 | Roman | 55/68 X |
| 4,542,010 | 9/1985 | Roman et al. | 55/68 X |
| 4,609,383 | 9/1986 | Bonaventura et al. | 55/16 |
| 4,654,053 | 3/1987 | Sievers et al. | 55/68 |
| 4,668,255 | 5/1987 | Govind | 55/68 X |
| 4,680,037 | 7/1987 | Ramprasad et al. | 55/16 |
| 4,705,544 | 11/1987 | Okita et al. | 55/16 X |
| 4,713,091 | 12/1987 | Govind | 55/68 X |
| 4,761,209 | 8/1988 | Bonaventura et al. | 55/68 X |
| 4,888,032 | 12/1989 | Busch | 55/68 X |
| 4,985,053 | 1/1991 | Sugie | 55/16 X |

FOREIGN PATENT DOCUMENTS

| | | | |
|---|---|---|---|
| 0186182 | 7/1986 | European Pat. Off. | 55/158 |
| 0304818 | 3/1989 | European Pat. Off. | 55/158 |
| 56-048246 | 5/1981 | Japan | 55/16 |
| 61-230708 | 10/1986 | Japan | 55/158 |
| 61-271005 | 12/1986 | Japan | 55/158 |
| 62-171730 | 7/1987 | Japan . | |
| 62-241551 | 10/1987 | Japan | 55/158 |
| 63-001422 | 1/1988 | Japan | 55/158 |
| 63-093789 | 4/1988 | Japan | 55/158 |
| 63-156565 | 6/1988 | Japan | 55/158 |
| 1-242124 | 9/1989 | Japan | 55/158 |
| 2-152529 | 6/1990 | Japan | 55/16 |

OTHER PUBLICATIONS

Tsuchida, The Chemical Society of Japan, 1988, No. 6, pp. 845–852.
"Composite Polymeric Membrane Containing Oxygen Carrier", Masanori Ikeda and Hirokazu Ohno, Proceedings, vol. 1, The 1990 International Congress on Membranes and Membrane Processes, ICOM '90, Chicago, U.S.A., 1990, pp. 667–669.

*Primary Examiner*—Robert Spitzer
*Attorney, Agent, or Firm*—Alvin H. Fritschler

[57] ABSTRACT

Oxygen-permeable polymeric complexes comprise (a) a transition metal (II) ion, (b) a liqand of meso-tris($\alpha$, $\alpha$,$\alpha$-o-substituted-amidophenyl)-mono-($\beta$-o-substituted amidophenyl) porphyrinato, and (c) an aromatic amine polymer.

8 Claims, No Drawings

OXYGEN-PERMEABLE POLYMERIC MEMBRANES

BACKGROUND OF THE INVENTION

This invention relates to oxygen-permeable polymeric membranes to be used in processes for producing oxygen- or nitrogen-enriched air for industrial, medical, and other applications. More particularly, the invention concerns polymeric membranes which contain, as dispersed therein, a metal complex capable of adsorbing and desorbing oxygen rapidly and reversibly.

Oxygen is one of the chemicals most widely used on industrial scales, specifically in the manufacture of iron, steel, and other metals and glass, in chemical oxidation and combustion, and in wastewater disposal. It has also very extensive usage in the field of medical care, including the therapy for lung disease patients by means of oxygen inhalation. Nitrogen, on the other hand, is a chemical conveniently and extensively used to maintain a nitrogen atmosphere, for example, for the preservation of foods, in fermentation processes, and in electronic circuit fabrication. For these reasons the development of processes for concentrating oxygen and nitrogen out of air is an important problem with far-reaching effects on various sectors of industry. While low-temperature and adsorption techniques are in use as industrial processes for atmospheric oxygen and nitrogen concentration, membrane separation is considered promising from the energy-saving viewpoint.

Success of membrane separation depends primarily on the discovery of a membrane material that would permit selective and efficient oxygen permeation relative to nitrogen from air. Currently available membranes capable of permeating and concentrating atmospheric oxygen (known as oxygen-permeable membranes) are those of silicone, silicone polycarbonate, and the like. Some of them are in practical service. They do not have high oxygen-permeation selectivity ($O_2/N_2$) value (oxygen-permeability coefficient/nitrogen-permeability coefficient), the value being approximately 2, and yet exhibit high permeability coefficient ($10^{-8}$[cm$^3$·(STP)·cm/cm$^2$·sec·cmHg]). With this feature the membranes are incorporated in modules, multi-stage processes, and other systems to obtain oxygen-enriched air, with oxygen concentrations of about 30%. In order to obtain highly oxygen-rich air useful for industrial and medical applications by a single, continuous permeable-membrane pass, it is essential that the membrane have an ($O_2/N_2$) value of at least 5.

The first requisite for an enhanced selectivity ($O_2/N_2$) is to make oxygen more soluble than nitrogen with respect to the membrane.

We have hitherto continued the synthesis of metal complexes capable of rapid, reversible adsorption and desorption of oxygen molecules. We clarified essential requirements of the metal complexes that can adsorb and desorb oxygen molecules selectively, rapidly, and reversibly, even in a solid-phase membrane polymer. We successfully synthesized the novel complexes and taught their use for oxygen-permeable membranes (Patent Application Public Disclosure No. 171730/1987).

Highly oxygen-rich air is useful for industrial and medical applications, and large quantities of highly nitrogen-rich air are used as inert gas in many sectors of industry. If they are to be obtained continuously by a single pass through an economical membrane, it is essential that the membrane have a selectivity ($O_2/N_2$) value of 5 or upwards.

We have hitherto continued the synthesis of metal complexes capable of rapid, reversible adsorption and desorption of oxygen molecules. As a result, we successfully synthesized novel metal complexes that can adsorb and desorb oxygen molecules selectively, rapidly, and reversibly, even in a solid phase. We further found that the metal complexes carried in polymeric solid-phase membranes are kept from irreversible oxidation and permit stable, selective permeation of oxygen.

However, polymeric membranes incorporating such complexes, when used in air permeation, did not always achieve the object satisfactorily in the region where the feed oxygen pressure was high (20 mmHg or above), although the ($O_2/N_2$) value exceeded the target value of 5. Thus, a further improvement in the ($O_2/N_2$) value was sought.

SUMMARY OF THE INVENTION

In view of the above, we have made further intensive research for the improvement in performance of the complex that can adsorb and desorb oxygen. We have now successfully synthesized a novel porphyrinato transition metal (II) complex, i.e., a meso-tris($\alpha,\alpha,\alpha$-o-substituted-amidophenyl)-mono-($\beta$-o-substituted amidophenyl)porphyrinato cobalt (II), represented by the formula (I):

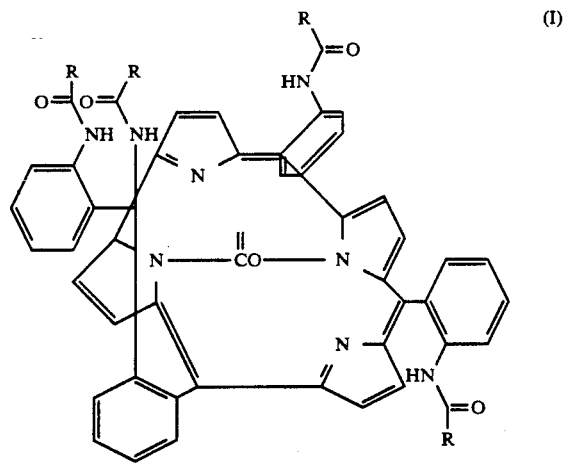

in which Co is the transition metal II, said transition metal II being more broadly referred to below by the letter M. The complex, when combined with a polymeric ligand, gives a membrane with desired oxygen permeation performance. In the complex of the formula (I), the transition metal (II) is preferably cobalt (II) and substituents R's are preferably acetyl, acryl, methacryl, or pival. Since one of the four substituents on the porphyrin of the complex faces downward, oxygen adsorption and desorption take place very rapidly through the steric interstices. In a solid membrane combining this complex with a copolymer of an alkyl acrylate or alkyl methacrylate and a vinyl aromatic amine, the life of the complex of the formula (I) for oxygen adsorption and desorption is extended sufficiently for practical use, and the concept has led to the present invention as oxygen-permeable polymeric membranes.

The invention thus resides in the following oxygen-permeable polymeric membranes:

1. An oxygen-permeable polymeric membrane characterized by a complex comprising (a) a transition metal (II) ion, (b) a ligand comprising a meso-tris($\alpha,\alpha,\alpha$-o-substituted-amidophenyl)-mono-($\beta$-o-substituted amidophenyl)porphyrinato, said metal ion and porphyrin being of the formula (I)

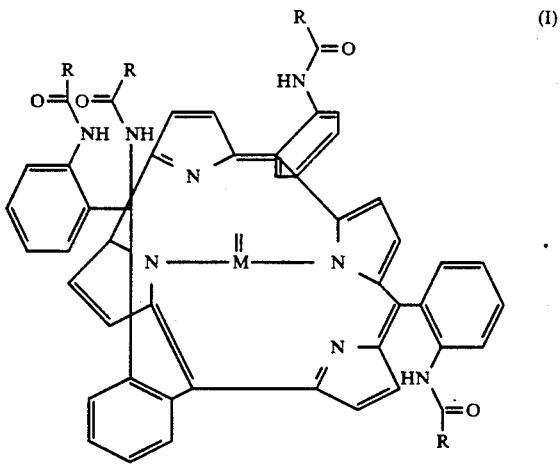

in which M stands for a transition metal (II), R's are a substituent each, being acetyl, acryl, methacryl, or pival, and (c) an aromatic amine polymer.

2. The membrane of 1 above in which said transition metal (II) comprises cobalt (II).

3. The membrane of 1 above in which said aromatic amine polymer comprises copolymers of a vinyl aromatic amine and either (a) an alkyl acrylate or (b) an alkyl methacrylate.

4. The membrane of 3 above in which said vinyl aromatic amine is either (1) vinylimidazole or (2) vinylpyridine.

5. The membrane of 3 above in which said alkyl group of the alkyl acrylate or alkyl methacrylate contains from 1 to 15 carbon atoms.

6. The membrane of 5 above in which said transition metal (II) ion comprises cobalt (II).

7. The membrane of 1 above in which said transition metal (II) and said ligand comprise from about 1 to 30% by weight of the polymeric membrane.

8. The membrane of 6 above in which said transition metal (II) and said ligand comprise from about 1 to 30% by weight of the polymeric membrane.

DETAILED DESCRIPTION OF THE INVENTION

Stable, reddish brown membranes were successfully made by uniformly dispersing the newly synthesized porphyrinato transition metal complexes, especially cobalt complexes, in monomeric bases under specific conditions. The ($O_2/N_2$) values of the membranes exceeded 5 even at a feed pressure of 150 mmHg. They could collect oxygen-rich air concentrated to 55% or upwards by single-step permeation of atmospheric air. At an oxygen feed pressure of 10 mmHg the ($O_2/N_2$) value was more than 10. In order that the complex permeate oxygen as efficiently in the region where the feed pressure is high, it is important that the rates of combination and dissociation of the complex and oxygen be great (Tsuchida: J. Japan Chem. Soc., 1988, pp. 845-852 (1988)). The reaction for combination of oxygen with the porphyrinato complex is influenced by the structure of the complex and is governed by the effect of the steric substituents of the porphyrin surface. The rate constant increases with the relaxation of the stereostructure over the rings of the porphyrin, with the result that the efficiency of oxygen permeation is improved and an increase in the ($O_2/N_2$) value is made possible.

Thus, the above findings have now led to the present invention. It provides novel oxygen-enriching polymeric membranes characterized in that a complex of a specific porphyrin structure is uniformly dispersed in a polymeric ligand.

The transition metal (II) ion, especially cobalt (II), forms a complex which has reversible interactions with $O_2$.

The aromatic amine functions as the axial base in the complex, "activating" the complex for reversible interactions with $O_2$.

For use in the present invention the porphyrinato transition metal complex is represented by the general formula (I) in which the transition metal is desired to be cobalt, and the substituents R's are desired to be acetyl, acryl, methacryl, or pival. If the Rs are larger than these, the molecular weight of the complex increases, reducing the amount of oxygen adsorbed or desorbed per unit weight of the complex and also lowering the rate of increase in the separability of the membrane itself. The core metal of the porphyrinato complex other than cobalt is, for example, iron, but the latter involves difficulties in preparing a membrane that retains activity. Desirable as the polymeric ligand is a copolymer (with a molecular weight of 100,000 to 300,000) of a vinyl aromatic amine and an alkyl acrylate or alkyl methacrylate in which the alkyl group contains from 1 to 15 carbon atoms, typified by poly(octyl methacrylate-co-N-vinylimidazole) or poly(octyl- methacrylate-N-vinylpyridine). If the alkyl group contains more than 16 carbon atoms, the resulting membrane will be brittle or hard to form. Also, if a ligand of a lower molecular weight is used, the membrane life for oxygen adsorption and desorption will be shortened.

The cobalt ion of the porphyrinato cobalt and the ligand residue (aromatic amine residue) that constitute a complex are in a molar ratio appropriately in the range from 1:1 to 1:30.

A porphyrinato cobalt and a polymeric ligand are separately dissolved uniformly in an organic solvent such as chloroform, thoroughly deoxidized, and mixed up. In this case the porphyrinato complex content is desirably chosen from the range of about 1 to about 30% by weight. If the content is less than 1% the selectivity ($O_2/N_2$) value will be too low to obtain sufficiently oxygen-enriched air, but a content of 31% or more will embrittle the resulting membrane or hardly form a membrane. The oxygen-permeable polymeric membrane of the invention is formed by so-called solvent casting, or a process in which the mixed solution is cast over a Teflon sheet or the like in an oxygen-free atmosphere and the solvent is allowed to evaporate slowly. For the manufacture of the membrane, thorough oxygen removal from the solution in advance is advisable.

The thickness of the oxygen-permeable membrane according to the invention is not specially limited but is usually chosen from the range of about 1 to about 100 $\mu$m. The membrane of the invention permits oxygen permeation with a high selectivity, at the ($O_2/N_2$) value of 10 or upwards. For example, air at an oxygen concentration of 70% or more can be obtained by single-stage concentration. The measurements of gas permeation through the oxygen-permeable membranes may be made using an ordinary gas permeability measuring instrument conforming to either the low vacuum method or the isotactic method.

EXAMPLES

The invention will be more fully described below in connection with examples thereof which, of course, are in no way limitative.

Also it is to be understood that although specifically dense membranes are deal with in the examples, the membranes of the invention are applicable as well to porous membranes without departing from the spirit and scope of the invention.

EXAMPLE 1

Meso-tris($\alpha,\alpha,\alpha$-o-methacrylamidophenyl)-mono-($\beta$-o-methacryl amidophenyl)porphyrinato cobalt (II) was synthesized in the following manner.

Meso-tris($\alpha,\alpha,\alpha$-o-aminophenyl)-mono-($\beta$-o-aminophenyl-)porphyrin, an isomer of meso-tetra(o-aminophenyl)porphyrin (5 g), was separated and purified (Rf=0.18, 2.5 g) using a silica gel column and chloroform/ether (4/1) solvent. 2.5 g of the separated meso-tris($\alpha,\alpha,\alpha$-o-aminophenyl)-mono-($\beta$-o-amino-phenyl)-porphyrin was dissolved in 100 ml of a chloroform solution. While the reactant solution was being kept at 0° C. or below, 12 ml triethylamine and 17 ml methacrylic acid chloride were added. After the reaction, the product was refined (Rf=0.41) using a silica gel column and a developing solvent chloroform/ether (8/1) to yield 3.1 g of meso-tris($\alpha,\alpha,\alpha$-o-methacrylamidophenyl) -mono-($\beta$-o-methacrylamidophenyl)- porphyrin, $^1$H NMR$\delta$ (ppm): $-2.7$ (s, 2H internal H), 1.1–1.2 (s, 12H, $-C(CH_2)=CH_3$), 4.3–4.5 (s, 8H, $-C(CH_2)=CH_3$), 7.1–7.9 (m, 16$\overline{H}$, phenyl-H), 8.7 (s, 4H, amide-H), 8.8 (s, 8H, pyrol, $\beta$-H).

Cobalt acetate and meso-tris($\alpha,\alpha,\alpha$-o-methacrylamido-phenyl)-mono-($\beta$-o-methacrylamidophenyl)porphyrin were dissolved in a mixed chloroform/methanol solution. After 15 hours of boiling-point reflux, the resultant was column-refined to obtain 1.7 g of meso-tris($\alpha,\alpha,\alpha$-o-methacrylamidophenyl)-mono-($\beta$-o-methacrylamidophenyl)porphyrinato cobalt (II).

A polymeric membrane was made in the following way. Nitrogen gas was introduced for 0.5 hour separately into 20 ml of a chloroform solution containing 10 mg meso-tris($\alpha,\alpha,\alpha$-o-methacrylamidophenyl)-mono-($\beta$-o-methacrylamidophenyl)porphy-rinato cobalt (II) (hereinafter called "$\alpha^3\beta$-CoMP" for brevity) and 100 ml of a chloroform solution containing 0.5 g poly(octylmethacrylate-co-N-vinylimidazole) (TFMIm). Using three-way tubes the two solutions were simultaneously deaerated under vacuum.

Following thorough deaeration, the solutions were mixed, and the solvent was subjected to pressure reduction under vacuum until the total amount of the mixed solution decreased to about 30 ml. Next, the solution under vacuum was transferred into a dry box, the box was swept out several times with nitrogen, and the solution under vacuum was cast over a tetrafluoroethylene sheet 7 cm by 7 cm in size in an open nitrogen atmosphere. The chloroform solution was gradually reduced in pressure inside the dry box, down to 60, 50, 30, and 10 cmHg over 40 hours. Finally, a polymeric membrane containing 12% by weight $\alpha^3\beta$-CoMP, 50 to 60 $\mu$m thick, red and clear, with adequate mechanical strength, was obtained.

Reversible oxygen adsorption and desorption of the porphyrinato complex in the membrane could be confirmed from changes in the visible spectrum (oxygen-combined type: 545 nm; deoxygenation type: 528 nm).

The polymeric membrane thus prepared was tested for air permeability in conformity with the low vacuum method. The membrane had a permeability coefficient of $4.0 \times 10^{-9} cm^3 \cdot (STP) \cdot cm/cm^2 \cdot sec \cdot cmHg$ and $O_2/N_2=10$, achieving efficient permeation of oxygen.

Reference values of a membrane using a complex meso-tetra-($\alpha,\alpha,\alpha,\alpha$-o-pivalamidophenyl)porphyrinato cobalt (II), tested under the same conditions as above, were $1.7 \times 10^9 (cm^3 \cdot (STP) \cdot cm/cm^2 \cdot sec \cdot cmHg$ and $O_2/N_2=4.3$. The reference value of a polymeric membrane free of the complex was $(O_2/N_2)=3.2$, clearly indicating the superior performance of the membrane according to the present invention.

EXAMPLE 2

A polymeric membrane, 50 to 60 $\mu$m thick, was made in the same manner as described in Example 1 with the exception that the $\alpha^3\beta$-CoMP was replaced by meso-tris($\alpha,\alpha,\alpha$-o-acrylamido-phenyl)-mono-($\beta$-o-acrylamidophenyl)porphyrinato cobalt (II).

Meso-tris($\alpha,\alpha,\alpha$-o-acrylamidophenyl)-mono-($\beta$-o-acrylamido-phenyl)porphyrinato cobalt (II) was synthesized in the following way.

In the same manner as in Example 1, meso-tris($\alpha,\alpha,\alpha$-o-aminophenyl)-mono-($\beta$-o-aminophenyl)porphyrin was purified (2.5 g). 2.5 g of the separated meso-tris-($a,\alpha,a$-o-aminophenyl)-mono-($\beta$-o-aminophenyl)porphyrin was dissolved in 100 ml of a chloroform solution. While the reactant solution was being kept at 0° C. or below, 12 ml triethylamine and 16 ml acrylic acid chloride were added. After the reaction, the resultant was column-refined to yield 2.6 g of meso-tris($\alpha,\alpha,\alpha$-o-acryl-amidophenyl)-mono-($\beta$-o-acrylamidophenyl)porphyrin, $^1$H NMR$\delta$(ppm): $-2.7$ (s, 2H internal H), 5.05.1 (s, 8H, $-CH-CH_2$), 5.8, 5.9, 6.0 (s, 4H, $-CH=CH_2$), 7.1–7.9 (m, 16H, phenyl-H), 8.6 (s, 4H, amide-$\overline{H}$), 8.9 (s, 8H, pyrol, $\beta$-H).

Cobalt acetate and meso-tris($\alpha,\alpha,\alpha$-o-acrylamidophenyl)-mono-($\beta$-o-acrylamidophenyl)porphyrin were dissolved in a mixed chloroform/methanol solution. After 15 hours of boiling-point reflux, the resultant was column-refined to obtain 0.82 g of meso-tris($\alpha,\alpha,\alpha$-o-acrylamidophenyl)-mono-($\beta$-o-acrylamido-phenyl)porphyrinato cobalt (II) (hereinafter called "$\alpha^3\beta$-CoArP").

A complex membrane containing 13% by weight $\alpha^3\beta$-CoArP was made in the same way as in Example 1. Reversible oxygen adsorption and desorption of the porphyrinato complex in the membrane could be confirmed from visible spectrum changes (oxygen-combined type: 545 nm; deoxygenation type: 528 nm).

The polymeric membrane thus prepared was tested for air permeability in conformity with the low vacuum method. The membrane had a permeability coefficient of $5.5 \times 10^{-9}$ $cm^3 \cdot (STP) \cdot cm/cm^2 \cdot sec \cdot cmHg$ and $O_2/N_2=14$, achieving efficient permeation of oxygen.

Reference values of a membrane using a complex meso-tetra-($\alpha,\alpha,\alpha,\alpha$-o-pivalamidophenyl)porphyrinato cobalt (II), tested under the same conditions as above, were: permeability coefficient $1.7 \times 10^{-9}$ $cm^3 \cdot (STP) \cdot cm/cm^2 \cdot sec \cdot cmHg$ and $(O_2/N_2)=4.3$. The reference value of a polymeric membrane free of the complex was $(O_2/N_2)=3.2$, clearly testifying to the superior performance of the membrane of the present invention.

EXAMPLE 3

The procedure of Example 1 was repeated excepting the use as the complex of meso-tris(α,α,a-o-acetamidophenyl)-mono-(β-o-acetamidophenyl)porphyrinato cobalt (II), and permeation measurements were made in the same manner as in Example 1.

The meso-tris(α,α,a-o-acetamidophenyl)-mono-(β-o-acet-amidophenyl)porphyrinato cobalt (II) was synthesized as below.

In the same manner as in Example 1, meso-tris(α,α,α-o-aminophenyl)-mono-(β-o-aminophenyl)porphyrin was purified (2.5 g). 2.5 g of the separated meso-tris-(a,α,a-o-aminophenyl)-mono-(β-o-aminophenyl)porphyrin was dissolved in 100 ml of a chloroform solution. While the reactant solution was being kept at 0° C. or below, 12 ml triethylamine and 14 ml acetyl chloride were added. After the reaction, the resultant was co-lumn-refined to yield 2.1 g of meso-tris(α,α,α-o-acetyl-amidophenyl)-mono-(β-o-acetylamidophenyl)porphyrin, $^1$H NMRδ(ppm): —2.5 (s, 2H internal H), 1.80–1.90(s, 12H, CH$_3$), 7.1–8.0 (m, 16H, phenyl-H), 8.7 (s, 4H, amide-H), 8.8 (s, 8H, pyrol, β-H).

Cobalt acetate and meso-tris(α,α,α-o-acrylamidophenyl)-mono-(β-o-acrylamidophenyl)porphyrin were dissolved in a mixed chloroform/methanol solution. After 10 hours of boiling-point reflux, the resultant was column-refined to obtain 0.45 g of meso-tris(α,α,α-o-acetylamidophenyl)-mono-(β-o-acetylamido-phenyl)-porphyrinato cobalt (II) (hereinafter called "α$^3$β-CoAtP").

A complex membrane containing 12% by weight α$^3$β-CoAtP was made in the same way as in Example 1. Reversible oxygen adsorption and desorption of the porphyrinato complex in the membrane could be confirmed from visible spectrum changes (oxygen-combined type: 545 nm; deoxygenation type: 528 nm).

The polymeric membrane thus prepared was tested for air permeability by the low vacuum method. The membrane had a permeability coefficient of $4.9 \times 10^{-9}$ cm$^3$·(STP)·cm/cm$^2$·sec·cmHg and O$_2$/N$_2$=12, achieving efficient oxygen permeation.

Reference values of a membrane using a complex meso-tetra-(α,α,α,α-o-pivalamidophenyl)porphyrinato cobalt (II), tested under the same conditions as above, were: permeability coefficient $1.7 \times 10^{-9}$ cm$^3$·(STP)·cm/cm$^2$·sec·cmHg and (O$_2$/N$_2$)=4.3. The reference value of a polymeric membrane free of the complex was (O$_2$/N$_2$)=3.2, clearly proving the superior performance of the membrane of the present invention.

EXAMPLE 4

In Example 1 the complex used was replaced by meso-tris-(α,α,a-o-pivalamidophenyl)-mono-(β-o-pivalamidophenyl)porphy-rinato cobalt (II), but otherwise in the same manner as in Example 1 permeation measurements were made.

The meso-tris(α,α,a-o-pivalamidophenyl)-mono-(β-o-pival-amidophenyl)porphyrinato cobalt (II) was synthesized in the following way.

As in Example 1, meso-tris(α,α,α-o-aminophenyl)-mono-(β-o-aminophenyl)porphyrin was purified (2.5 g). 2.5 g of the separated meso-tris(a,α,a-o-aminophenyl)-mono-(β-o-aminophenyl)-porphyrin was dissolved in 100 ml of a chloroform solution. While the reactant solution was being kept at 0° C. or below, 12 ml triethylamine and 18 ml acetyl chloride were added. After the reaction, the resultant was column-refined to yield 3.7 g of meso-tris(α,α,α-o-pivalamidophenyl)-mono-(β-o-pivalamido-phenyl)porphyrin, $^1$H NMRδ (ppm): —2.5 (s, 2H internal H), 0.10, 0.16, 0.23 (s, 27H, tert CH$_3$), 7.1–7.9 (m, 16H, phenyl-H), 8.7 (s, 4H, amide-H), 8.8 (s, 8H, pyrol, β-H).

Cobalt acetate and meso-tris(α,α,α-o-pivalamidophenyl)-mono-(β-o-pivalamidophenyl)porphyrin were dissolved in a mixed chloroform/methanol solution. After 20 hours of boiling-point reflux, the resultant was column-refined to obtain 3.1 g of meso-tris(α,α,α-o-pivalamidophenyl)-mono-(β-o-pivalamido-phenyl)porphyrinato cobalt (II) (hereinafter called "α$^3$β-CoPP").

A complex membrane containing 12% by weight α$^3$β-CoPP was made in the same way as in Example 1. Reversible oxygen adsorption and desorption of the porphyrinato complex in the membrane could be confirmed from visible spectrum changes (oxygen-combined type: 545 nm; deoxygenation type: 528 nm).

The polymeric membrane thus prepared was tested for air permeability by the low vacuum method. The membrane had a permeability coefficient of $3.5 \times 10^{-9}$ cm$^3$·(STP)·cm/cm$^2$·sec·cmHg and O$_2$/N$_2$=8.8, achieving efficient oxygen permeation.

Reference values of a membrane using a complex meso-tetra-(α,α,α,α-o-pivalamidophenyl)porphyrinato cobalt (II), tested under identical conditions, were: permeability coefficient $1.7 \times 10^{-9}$ cm$^3$·(STP)·cm/cm$^2$·sec·cmHg and (O$_2$/N$_2$)=4.3. The reference value of a polymeric membrane free of the complex was (O$_2$/N$_2$)=3.2, clearly proving the superior performance of the membrane of the present invention. Also, the oxygen permeability of the membrane according to the invention was generally as stable as the conventional membranes.

What is claimed is:

1. An oxygen-permeable polymeric membrane characterized by a complex comprising (a) a transition metal (II) ion, (b) a ligand comprising a meso-tris(α,α,α-o-substituted-amidophenyl)-mono-(β-o-substituted amidophenyl)porphyrinato, said metal ion and porphyrin being of the formula (I)

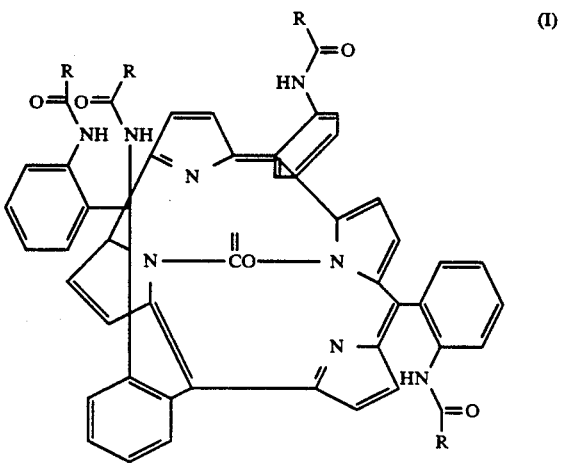

in which R's are a substituent each, being acetyl, acryl, methacryl, or pival, and (c) an aromatic amine polymer.

2. An oxygen-permeable polymeric membrane characterized by a complex comprising (a) a transition metal (II) ion, (b) a ligand comprising a meso-tris(α,α,α-o-substituted-amidophenyl)-mono-(β-o-substituted amidophenyl)porphyrinato, said metal ion and porphyrin being of the formula (I)

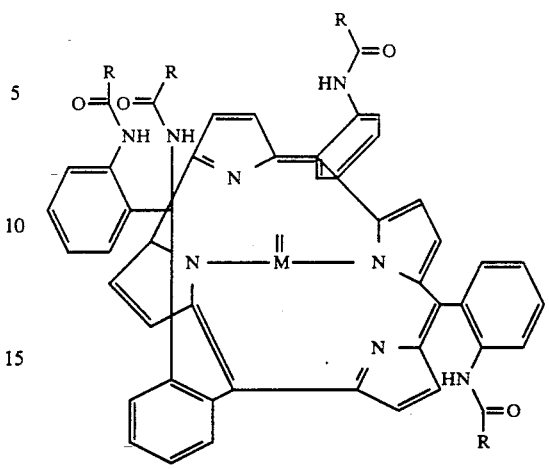

in which M stands for a transition metal (II), R's are a substituent each, being acetyl, acryl, methacryl, or pival, and (c) an aromatic amine polymer.

3. The membrane of claim 2 in which said aromatic amine polymer comprises copolymers of a vinyl aromatic amine and either (a) an alkyl acrylate or (b) an alkyl methacrylate.

4. The membrane of claim 3 in which said vinyl aromatic amine is either (1) vinylamidazole or (2) vinylpyridine.

5. The membrane of claim 3 in which said alkyl group of the alkyl acrylate or alkyl methacrylate contains from 1 to 15 carbon atoms.

6. The membrane of claim 5 in which said transition metal (II) ion comprises cobalt (II).

7. The membrane of claim 6 in which said transition metal (II) and said ligand comprise from about 1 to 30% by weight of the polymeric membrane.

8. The membrane of claim 2 in which said transition metal (II) and said ligand comprise from about 1 to 30% by weight of the polymeric membrane.

* * * * *